United States Patent
Verbeck, IV et al.

(10) Patent No.: US 10,813,585 B2
(45) Date of Patent: Oct. 27, 2020

(54) TECHNIQUES FOR RAPID DETECTION AND QUANTITATION OF VOLATILE ORGANIC COMPOUNDS (VOCS) USING BREATH SAMPLES

(71) Applicants: University of North Texas, Denton, TX (US); Inspectir Systems, LLC, Frisco, TX (US)

(72) Inventors: Guido Fridolin Verbeck, IV, Lewisville, TX (US); John Redmond, Frisco, TX (US); Tim Wing, Frisco, TX (US)

(73) Assignee: The University of North Texas, Denton, TX (US)

( * ) Notice: Subject to any disclaimer, the term of this patent is extended or adjusted under 35 U.S.C. 154(b) by 0 days.

(21) Appl. No.: 16/715,576

(22) Filed: Dec. 16, 2019

(65) Prior Publication Data

US 2020/0178891 A1    Jun. 11, 2020

Related U.S. Application Data

(63) Continuation of application No. PCT/IB2019/056456, filed on Jul. 29, 2019.
(Continued)

(51) Int. Cl.
*A61B 5/00* (2006.01)
*A61B 5/08* (2006.01)
(Continued)

(52) U.S. Cl.
CPC ............ *A61B 5/4845* (2013.01); *A61B 5/082* (2013.01); *A61B 5/097* (2013.01); *A61B 10/00* (2013.01);
(Continued)

(58) Field of Classification Search
CPC ....... A61B 5/4845; A61B 10/00; A61B 5/082; A61B 5/097; A61B 2010/0087; G01N 33/948
(Continued)

(56) References Cited

U.S. PATENT DOCUMENTS

| 6,248,078 B1 * | 6/2001 | Risby ..................... A61B 5/097 600/529 |
| 2012/0302907 A1 * | 11/2012 | Palmskog ................. G01J 3/44 600/532 |

(Continued)

FOREIGN PATENT DOCUMENTS

WO    WO-2011029889 A1    3/2011

OTHER PUBLICATIONS

International Search Report and Written Opinion issued for PCT Application No. PCT/IB2019/056456, dated Dec. 20, 2019, 9 pages.

*Primary Examiner* — Marrit Eyassu
(74) *Attorney, Agent, or Firm* — Norton Rose Fulbright US LLP

(57) ABSTRACT

An exemplary breath analysis system may include a sampling chamber having a molecule collector disposed therein. The molecule detector may be configured such that volatile organic compounds (VOCs) present in a breath sample introduced to the sampling chamber adhere to the molecule collector. A heating element may introduce heat within the sampling chamber, causing release of at least a portion of the VOCs adhered to the molecule collector. An analysis device (e.g., a mass spectrometer or tetrahertz (THz) spectrometer) may identify one or more target VOCs from among at least the portion of the VOCs released from the molecule collector and generate an output representative of the identified one or more target VOCs. The output may include informa-
(Continued)

tion that quantitates a concentration of the one or more target VOCs with respect to a source of the breath sample.

15 Claims, 13 Drawing Sheets

Related U.S. Application Data

(60) Provisional application No. 62/712,941, filed on Jul. 31, 2018.

(51) Int. Cl.
*A61B 5/097* (2006.01)
*A61B 10/00* (2006.01)
*G01N 33/94* (2006.01)

(52) U.S. Cl.
CPC .... *G01N 33/948* (2013.01); *A61B 2010/0087* (2013.01)

(58) Field of Classification Search
USPC ........................................................ 73/23.23
See application file for complete search history.

(56) References Cited

U.S. PATENT DOCUMENTS

| | | | |
|---|---|---|---|
| 2014/0288454 A1* | 9/2014 | Paz .................... | A61B 5/4845 600/532 |
| 2015/0305651 A1* | 10/2015 | Attariwala ............ | A61B 5/082 600/532 |
| 2016/0363582 A1 | 12/2016 | Blackley | |
| 2017/0023453 A1* | 1/2017 | Hill, Jr. ................ | G01N 1/4022 |
| 2017/0074857 A1* | 3/2017 | Dennis ................ | A61B 5/0836 |
| 2017/0143933 A1* | 5/2017 | Pasadilla ................ | A62B 9/003 |
| 2018/0056302 A1 | 3/2018 | Ahmad et al. | |

\* cited by examiner

TECHNIQUES FOR RAPID DETECTION AND QUANTITATION OF VOLATILE ORGANIC COMPOUNDS (VOCS) USING BREATH SAMPLES

CROSS REFERENCE TO RELATED APPLICATION

This application is a 35 U.S.C. § 111(a) continuation of PCT Application No. PCT/IB2019/056456, filed Jul. 29, 2019, which claims the benefit of priority of U.S. Provisional Patent Application No. 62/712,941, filed Jul. 31, 2018, which are hereby incorporated by reference in their entirety.

TECHNICAL FIELD

The present application relates to breathalyzer systems and devices. More specifically the present application relates to breathalyzer systems and devices designed to facilitate quantitative analysis of THC and other substances in the field using breath samples.

BACKGROUND

Marijuana legalization has created many judicial issues and raises concerns of safety for civilians. Daily marijuana users have increased from 9.8% of the population of the United States in 2007, to 13.39% in 2014. While this is only a 3.6% increase, the potency of Δ-9-Tetrahydrocannabinol (Δ-9-THC), the psychoactive substance in marijuana, has also increased from 5% in 2001 to over 20% in marijuana leaves and over 60% in crude extracts. The increase in potency has led to an increase in crime reports for the local population. Specifically, areas with a high density of marijuana dispensaries had higher rates of property crime among all states with dispensaries. Another problem with marijuana legalization is the influence of marijuana while operating an automobile. Marijuana users are 25% more likely to be in an automobile accident than a sober driver, and more than 10% of all drivers on the weekend are under the influence of an illegal drug. As marijuana becomes legalized in more states, proper quantitation of Δ-9-THC is required, such that an accurate and rapid determination of whether a person is under the influence of marijuana can be achieved. This will also aid the judicial system in having a device that can accurately determine a concentration, allowing a set limit of Δ-9-THC to be determined for operating a vehicle.

Three cannabinoid compounds are currently analyzed to determine cannabinoid concentrations in the blood; they are Δ-9-THC, 11-hydroxy-tetrahydrocannabinol (11-OH-THC), and carboxy-tetrahydrocannabinol (THC-COOH). Currently, techniques for determining the presence of drugs, such as cannabinoids, require analysis via a blood, blood plasma, urine, or oral fluid samples. Most analytical techniques use gas chromatography coupled to mass spectrometry (GC/MS). This presents a problem of having to collect a sample and bring it back to the lab for further analysis. These techniques have a long analysis time, with most analyses taking more than 15 minutes to detect the cannabinoids. Furthermore, detecting Δ-9-THC using GC/MS can also introduce another problem because the ionization source is electron ionization (EI). Cannabidiol (CBD), an extracted resin from the hemp plant, has the same molecular weight as Δ-9-THC, as well as the same mass spectrum fragmentation patterns when ionized using electron ionization. Under the controlled substances act, CBD is classified as a Schedule I drug because of it being a derivative of marijuana. However, the agricultural act of 2014 allows industrial hemp to be cultivated and sold for purposes of marketing research. Some states view this bill as the right to contract agriculturalists to sell CBD legally. This creates a challenge in quantifying the amount of Δ-9-THC in person's breath because the signal may be a result of CBD in the person's breath, which they may have obtained legally.

Laws for legal limits of Δ-9-THC in the body have been established in some states. Twelve states have the zero-tolerance policy, which states that no person should have any cannabinoids their blood while driving. However, five states allow the use of medical marijuana. This causes an issue for patients getting treatment and then having to drive later in the day or later in the week because they could be considered to driving under the influence of marijuana (DUIM). The analytical techniques that test for all three cannabinoids can be problematic because THC-COOH, which is not psychoactive, remains in the blood long after both Δ-9-THC and 11-OH-THC remain in the blood. A person can fail a cannabinoid test even though they are experiencing no psychoactive effects. Other states have adopted per se blood cannabis content (BCC) laws. These select states each have their own limit with the overall range being between 1 nanogram of THC to milliliter of blood (ng/ml) to 5 ng/ml. If the person driving has a concentration higher than those values, they are deemed DUIM, which carries similar penalties to driving while intoxicated. Unfortunately, a device that can accurately and rapidly detect Δ-9-THC concentrations has yet to be developed.

Detecting cannabinoids from the breath of a person is needed to allow a non-invasive rapid determination in the field. Previous methods of breath determination of cannabinoids originate back to 1972, when marijuana was detected in the breath of people under the influence using a colorimetric test. This test collected breath and used a series of reactions with quinone-4-haloimine, 2,6-dihaloquinone-4-haloimine, sodium hydroxide, and ammonia to determine if the breath sample would change to a blue or red color. These colorimetric tests had to be done in large reaction vessels, had a broad range of colors representing a positive result, and required at least 1 microgram of THC in the breath to have a positive reaction. These tests were not capable of quantitating the level of Δ-9-THC, nor were they able to be used in the field.

Currently, three types of breathalyzers are being used by local law enforcement officers in the field, liquid chromatography coupled to mass spectrometry (LC/MS), high-field asymmetric waveform ion mobility (FAIMS), and liquid chromatography coupled to spectroscopy. A first company, Sensabues, utilizes a breath sampling kit. The person breathes into the sampling chamber and then the apparatus is sent back to the lab to be analyzed using LC/MS. While this method is useful for quantitation, it cannot be used in the field, which hinders this method. In addition, LCMS requires several minutes to analyze the sample once it has reached the lab before the cannabinoids can be seen. Two other companies provide systems that are capable of in field measurements. Cannabix Technologies Inc. has worked with the Yost research group at University of Florida to create a portable breathalyzer for Δ-9-THC that utilizes high-field asymmetric waveform ion mobility spectrometry (FAIMS). This device can analyze samples in a two-minute time window and can detect and quantitate Δ-9-THC in the sample at concentrations of 10 parts per million (ppm). While this device overcomes the portability issue, FAIMS does not contain the same resolution or peak capacity that is necessary for determining the concentration of Δ-9-THC. Without the proper resolution, the instrument would not be able to distinguish the compounds of tobacco smoke from cannabis smoke. Furthermore, without the peak capacity, other compounds, such as illicit drugs may be overlooked, allowing the driver to continue driving while under the influence of a different illicit substance. Another company, Hound Labs Inc., has developed a handheld instrument that also utilizes liquid chromatography coupled to spectroscopy to detect for the presence of Δ-9-THC by linking a fluorescent adduct to the para-position of the Δ-9-THC molecule. This device only requires picogram quantities of Δ-9-THC and works by capturing the breath of the person and condensing the breath onto C18 media. The media is then delivered to a TLC plate, where a solvent mixture is administered and after several minutes the fluorescent label is placed on the entire TLC plate. The fluorescent label will bind specifically to the Δ-9-THC, which is then excited using a diode-pumped solid-state laser. This excited state will cause a shift in the spectrum and can be referenced to a known Δ-9-THC sample. This method requires more than 8 minutes to analyze a sample and requires the use of a known reference every time an analysis takes place.

Since the turn of the century the number of synthetic opioid overdoses of civilians have risen 200% and from the years 2014-2016 50% of all drug overdoses were attributed to opioids. Military personnel have also had an increase in opioid overdoses as military emergency departments have recorded a steady rise of opioid overdoses increasing from 27% to 42% during the years of 2009-2012. With so many opioid overdoses occurring among both civilians and military personnel a need for improved detection methods is warranted. Most drug enforcement agencies can only analyze the opioid using gas chromatography coupled to mass spectrometry (GC/MS) or liquid chromatography to mass spectrometry (LC/MS). Opioids such as methadone and fentanyl are immediately hydroxylated upon entering the human body. This process of hydroxylation begins a metabolic cycle that creates volatile organic compounds (VOCs) such as propionic acid. Previous methods used to detect these VOCs have been with solid phase micro extraction (SPME) techniques coupled to GC/MS. Unfortunately, these methods require long equilibration times of up to 10 minutes.

SUMMARY

Systems, apparatuses, methods, and computer-readable storage media providing techniques for improved on-site quantitation of cannabinoids and other substances from breath samples are disclosed. Exemplary breath analysis systems and apparatuses of the present disclosure may include a sampling chamber having an inlet configured to receive a breath sample and provide the breath sample to the sampling chamber. A molecule collector may be disposed within the sampling chamber. The molecule detector may be configured such that volatile organic compounds (VOCs) present in the breath sample introduced to the sampling chamber adhere to the molecule collector. The breath analysis systems and apparatuses may include a heating element configured to introduce or induce heat within the sampling chamber, which may cause resorption of at least a portion of the VOCs adhered to the molecule collector. The exemplary breath analysis systems and apparatuses may include an analysis device configured to identify one or more target VOCs from among at least the portion of the VOCs released from the molecule collector and generate an output representative of the identified one or more target VOCs. The output may include information that quantitates a concentration of the one or more target VOCs with respect to a source of the breath sample with respect to the breath sample provided to the sampling chamber. In aspects, the analysis device may identify the one or more target VOCs using a mass spectrometer or tetrahertz (THz) spectrometer.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION

Various features and advantageous details are explained more fully with reference to the non-limiting embodiments that are illustrated in the accompanying drawings and detailed in the following description. Descriptions of well-known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Figure 1:
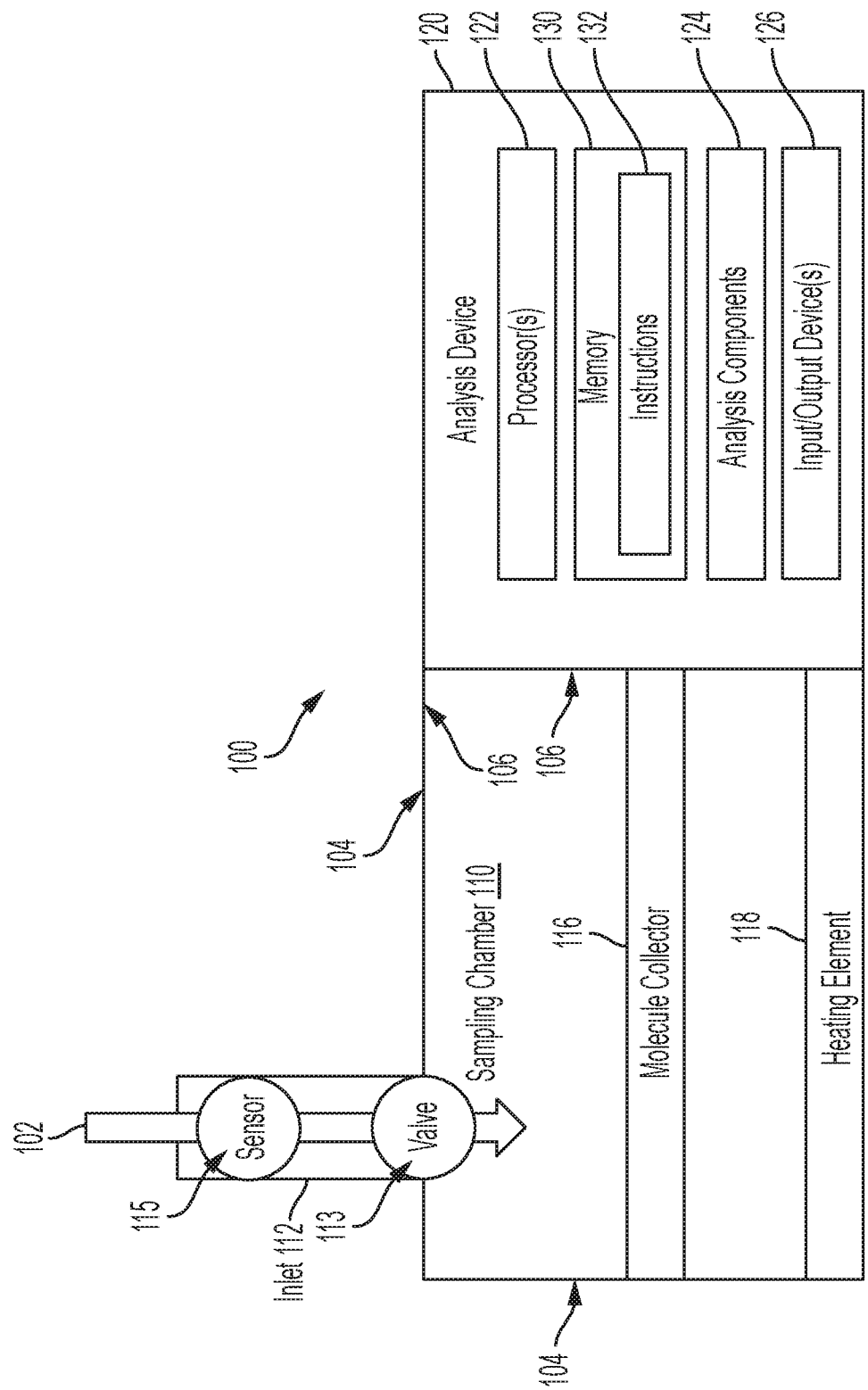
FIG. 1 illustrates a block diagram of a system for analyzing breath samples in accordance with aspects of the present disclosure.

Referring to FIG. 1, a block diagram of a system for analyzing breath samples in accordance with aspects of the present disclosure is shown as a system 100. As shown in FIG. 1, the system 100 includes a sampling chamber 110 and an analysis device 120. In aspects, the sampling chamber 110 may be configured as a removable and/or disposable component of the system 100. In such an arrangement, the sampling chamber 110 may be removably coupled to the analysis device 120. Configuring the sampling chamber 110 as a removable component of the system 100 may prevent contamination of consecutive breath samples analyzed by the analysis device 120. For example, a first sampling chamber may be utilized to perform analysis of a breath sample provided by a first person and a second sampling chamber may be utilized to perform analysis of a breath sample provided by a second person. Using different sampling chambers for different breath samples prevents one breath sample from potentially contaminating another breath sample. Where the sampling chamber(s) 110 is configured as a disposable component, the sampling chamber may be discarded after use or after a desired time has elapsed, such as an amount of time required by a law enforcement agency to retain the sampling chamber (e.g., for evidentiary purposes). Where the sampling chamber(s) 110 is configured as a reusable component, the sampling chamber 110 may be cleaned and prepared for subsequent reuse as needed. In aspects, a portion of the analysis device 120 may also be configured as a disposable and/or reusable component, such as portions of the analysis device 120 that may become contaminated if utilized to analyze multiple breath samples. In an aspect, the sampling chamber may be configured as a cartridge that may be utilized to obtain a breath sample and then placed within or coupled to the sampling device 120 for analysis. For example, the analysis device 120 may be installed in a law enforcement vehicle and a law enforcement official may have a person suspected of DUIM provide a breath sample to the cartridge, and then couple the cartridge to the analysis device 120 to facilitate analysis in accordance with aspect of the present disclosure. It is noted that the exemplary configurations described above have been provided for purposes of illustration, rather than by way of limitation and that numerous other ways for arranging, coupling, and/or integrating components of breath analysis systems in accordance with the present disclosure may be utilized.

As shown in FIG. 1, the sampling chamber 110 may comprise a housing having an outer surface 104 and an inner surface 106. The inner surface 106 of the housing may define a volume of the sampling chamber. An inlet 112 may be coupled to the sampling chamber 110. The inlet 112 may be configured to receive a breath sample 102 and to provide the breath sample 102 to the sampling chamber 110, and more specifically to provide the breath sample 102 to the volume of the sampling chamber. In aspects, a disposable mouthpiece (not shown in FIG. 1) may be removably coupled to a first end of the inlet 112 and a second end of the inlet 112 may be coupled to the sampling chamber 110. Alternatively, the first end of the inlet 112 may be utilized as the mouthpiece and the second end of the inlet 112 may be coupled to the sampling chamber 110. A valve 113 may be disposed within an air flow path between the inlet 112 and the sampling chamber 110. The valve 112 may be configurable to at least a first state and a second state. The first state may correspond to an open state configured to allow the breath sample 102 to flow into the sampling chamber 110 and the second state may correspond to a closed state configured to prevent contamination of the breath sample 102, such as by preventing ambient air from entering the sampling chamber 110 once the breath sample 102 has been provided. In an aspect, the sampling chamber 110 may include an outlet configured to release non-VOCs from the sampling chamber 110, as illustrated and described below with reference to FIG. 4A. The system 100 may also include a sensor 115 configured to determine whether the breath sample satisfies one or more criterion. For example, the sensor 115 may be configured to determine whether the breath sample 102 was exerted with sufficient force, has sufficient volume, etc., which may ensure that the breath sample 102 is sufficient for facilitating analysis in accordance with aspects of the present disclosure.

A molecule collector 116 may disposed within the sampling chamber 110. At least a portion of the molecule collector 116 may be disposed within the volume of the sampling chamber 110. The molecule collector 116 may be configured to adhere to volatile organic compounds (VOCs) present in the breath sample. For example, the molecule collector 116 may be constructed of materials such as Carboxen®. It is noted that the molecule collector 116 may be formed from a single material (e.g., one of the above-described materials), or may be formed from multiple materials, such as a base material that has been coated with one or more of the above-described materials. In aspects, the molecule collector 116 may have a solid form factor, such as a plate or rod formed from the materials mentioned above, or may have another form factor, such as a mesh formed from the materials mentioned above. The sampling device 110 may also include or be coupled to a heating element 118 configured to introduce heat within the sampling chamber 110. For example, the heating element 118 may include a power source coupled to the molecule collector 116 and configured to apply a voltage to the molecule collector 116. Applying the voltage to the molecule collector 116 may heat up the molecule collector, thereby introducing heat within the sampling chamber 110. As described in more detail below, the heat introduced within the sampling chamber 110 may cause the VOCs adhered to the molecule collector 116 to be released within the volume of the sampling chamber, thereby facilitating analysis and identification of one or more of the VOCs present within the sampling chamber 110.

The system 100 may include an analysis device. The analysis device 120 may be configured to identify one or more target VOCs from among the VOCs present in the sampling chamber 110 subsequent to release of at least a portion of the VOCs from the molecule collector 116 (e.g., due to the heat provided or introduced by the heating element 118). Additionally, the analysis device 120 may be configured to generate an output representative of the one or more target VOCs. As shown in FIG. 1, the analysis device 120 may include one or more processors 122, a memory 130, analysis components 124, and one or more input/output (I/O) devices 126. The memory 130 may store instructions 132 that, when executed by the one or more processors 122, cause the one or more processors 122 to control operations of the analysis device 120 and possibly other components of the system 100, such as the heating element 118, with respect to analyzing and identifying one or more target VOCs of the breath sample 102. The one or more target VOCs may include Δ-9-Tetrahydrocannabinol (Δ-9-THC), THC metabolites, opioids, opioid metabolites, or a combination thereof.

The I/O devices 126 may include switches, buttons, lights, display devices, or other control elements configured to receive inputs and/or provide outputs in connection with operation of the system 100. For example, switches and/or buttons may be provided to power the system 100 on and off, indicate that a breath sample has been provided, identify one or more target VOCs to be identified, or other functionality and control features. Lights may be provided to indicate: the system 100 is powered on or off, indicate whether the breath sample provided is satisfactory (e.g., based on information received from the sensor 115), indicate the identified VOCs (e.g., different lights may be associated with different VOCs that may be identified by the system 100), or to provide other information associated with operation of the system 100. One or more display devices may additionally be provided to display information, such as to indicate the identified VOCs, indicate an operational state of the system 100 (e.g., provide information indicating one or more of the different features described above with respect to the lights or other status information), and the like. The analysis component 124 may include a mass spectrometer or a tetrahertz (THz) spectrometer configured to identify the one or more target VOCs of the breath sample 102.

Figure 2:
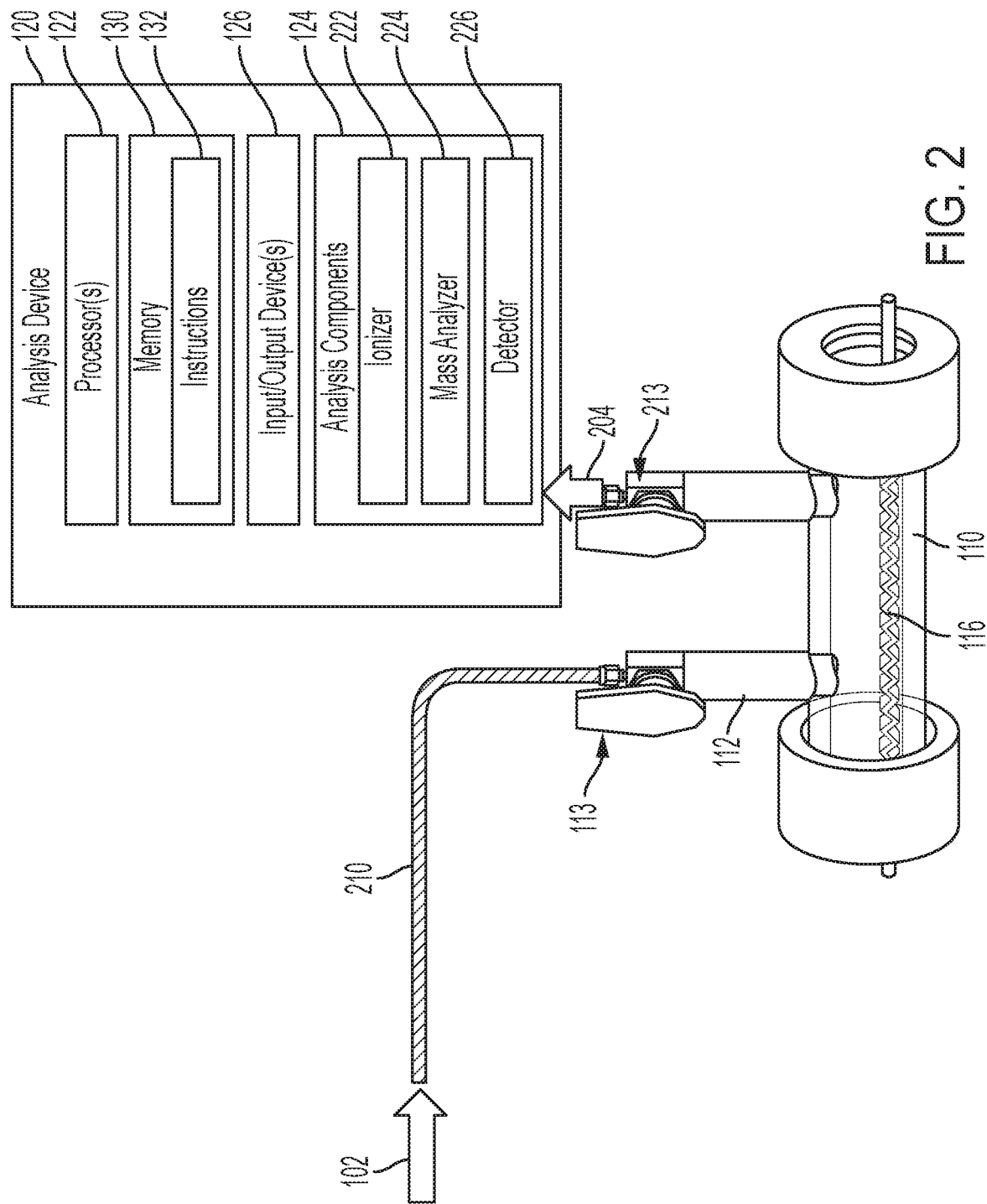
FIG. 2 illustrates a diagram of a mass spectrometer-based system for analyzing breath samples in accordance with aspects of the present disclosure.

Referring to FIG. 2, exemplary aspects of a system 100 utilizing mass spectrometer-based analysis components are illustrated. It is noted that in FIGS. 1 and 2, like reference numbers are utilized to refer to similar components. As shown in FIG. 2, the analysis components 124 may include an ionizer 222, a mass analyzer 224, and a detector 226. As described above, a breath sample 102 may be provided to the inlet 112 via a mouthpiece 210 when the valve 113 is in an open state. Subsequent to the breath sample 102 being provided to the volume of the sampling chamber 110, the heating element 118 (not shown in FIG. 2) may be activated, causing resorption of the VOCs adhered to the molecule collector 116. An outlet 204 may be utilized to provide the released VOCs to the analysis components 124. A valve 213 may be configurable to a first state (e.g., an open state) and a second state (e.g., a closed state) to control the providing of the VOCs to the analysis components. For example, in the first state, the VOCs may be allowed to pass through the outlet 204 to the analysis components 124 and in the second state, the VOCs may be prevented from passing through the outlet 204 to the analysis components 124. The ionizer 222 may be configured to ionize at least the portion of the VOCs released from the molecule collector to produce one or more ionized fragments. The mass analyzer 224 may be configured to separate the one or more ionized fragments (e.g., according to a mass-to-charge ratio of the one or more ionized fragments) and the detector 226 may be configured to identify the one or more target VOCs based on the separated one or more ionized fragments. In an aspect, the mass spectrometer components (e.g., the ionizer 222, the mass analyzer 224, and the detector 226) may operate under control of, or in coordination with, a computing device, such as a computing device that includes the one or more processors 122, the memory 130, and the one or more I/O devices 126. For example, the computing device may receive information from the mass spectrometer components, such as information associated with the one or more target VOCs identified in the breath sample 102, and may generate the output representative of the one or more target VOCs based on information associated with the one or more target VOCs. Additionally, the computing device may be configured to display the output at an output device, such as a display device.

Figure 3:
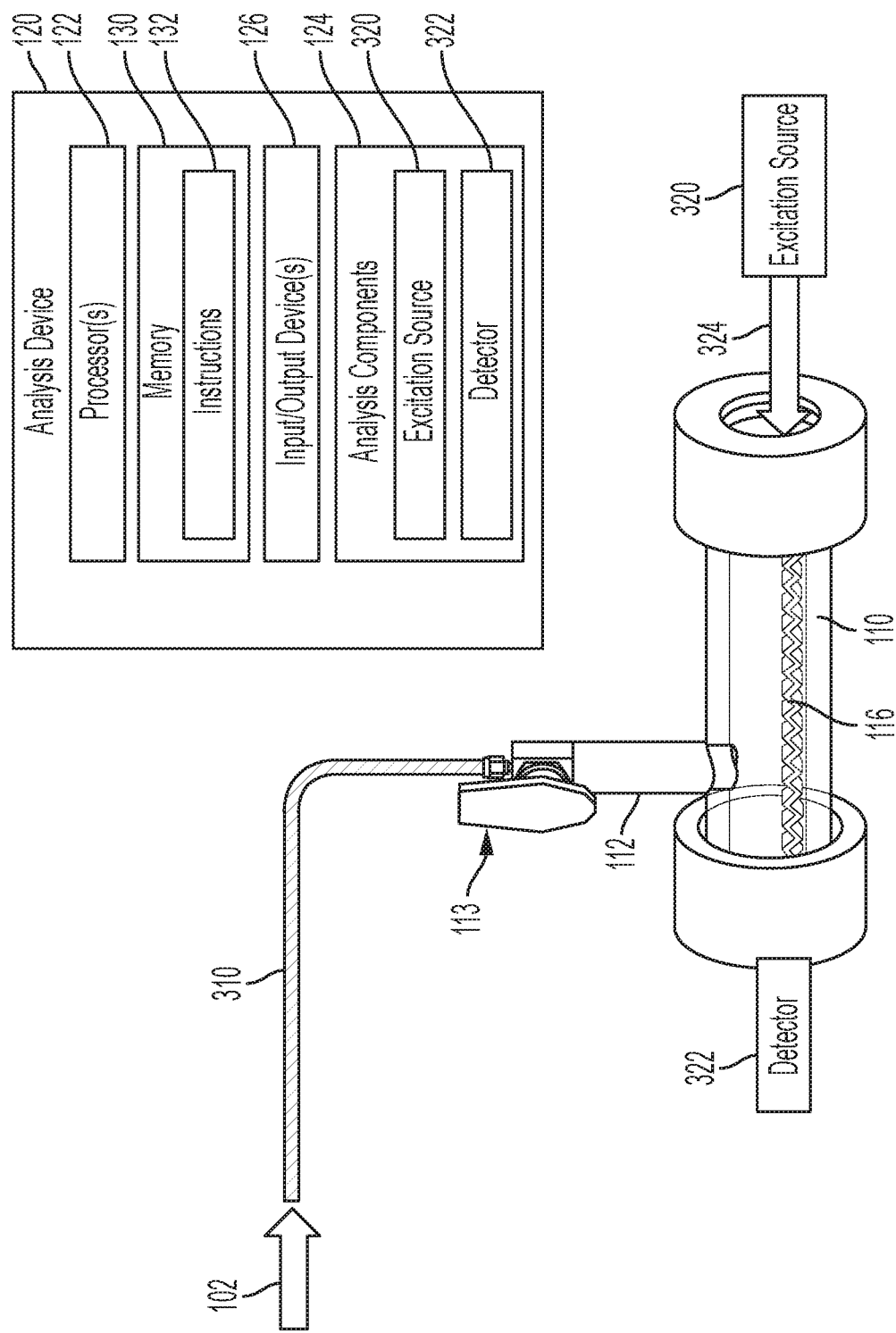
FIG. 3 illustrates a diagram of a Terahertz spectrometer-based system for analyzing breath samples in accordance with aspects of the present disclosure.

Referring to FIG. 3, exemplary aspects of a system 100 utilizing THz spectrometer-based analysis components is illustrated. It is noted that in FIGS. 1 and 3, like reference numbers are utilized to refer to similar components. As shown in FIG. 2, the analysis components 124 may include an excitation source 320 and a detector 322. As described above, a breath sample 102 may be provided to the inlet 112 via a mouthpiece 310 when the valve 113 is in an open state. Subsequent to the breath sample 102 being provided to the volume of the sampling chamber 110, the heating element 118 (not shown in FIG. 3) may be activated, causing resorption of the VOCs adhered to the molecule collector 116. The excitation source 320 may be configured to introduce an excitation signal 324 within the sampling chamber subsequent to the release of at least a portion of the VOCs from the molecule collector 116 and the detector 322 may be configured to identify the one or more target VOCs based on one or more characteristics associated with excitation of at least the portion of the VOCs released from the molecule collector 116 in response to the excitation signal 324. In an aspect, the excitation source 320 may be a THz laser device and the excitation signal 324 may be a THz laser signal. In aspects, the one or more characteristics associated with the excitation of at least the portion of the VOCs may include at least one of an absorbance characteristic and a fluorescent emission characteristic, which may be utilized to identify the one or more target VOCs present within the breath sample 102, as described in more detail below. In an aspect, the THz spectrometer components (e.g., the excitation source 320 and the detector 322) may operate under control of, or in coordination with, a computing device, such as a computing device that includes the one or more processors 122, the memory 130, and the one or more I/O devices 126. For example, the computing device may receive information from the THz spectrometer components, such as information associated with the one or more target VOCs identified in the breath sample 102, and may generate the output representative of the one or more target VOCs based on information associated with the one or more target VOCs. Additionally, the computing device may be configured to display the output at an output device, such as a display device.

Referring back to FIG. 1, the output representative of the one or more target VOCs may include information that quantitates a concentration of the one or more target VOCs with respect to a source of the breath sample. This information may facilitate a determination of whether a source of the breath sample, such as a person that provided the breath sample 102, is impaired or under the influence of one or more substances (e.g., substances corresponding to the identified one or more target VOCs). By providing information that quantitates the concentration of the one or more target VOCs, more accurate determinations of whether the source is impaired or under the influence of substances may be determined. Additionally, the techniques utilized by the system 100 (as configured in accordance with either FIG. 2 or FIG. 3) may facilitate more rapid identification and quantitation of the VOC levels, thereby facilitating in field determinations as to whether source is impaired or under the influence of one or more substances, such as THC. For example, unlike existing systems capable of quantitatively analyzing certain VOCs, which take a long time to complete, the system 100 may facilitate determination and quantization of VOCs in a few seconds, thereby facilitating practical use in the field, such as by law enforcement officials.

Figure 4A:
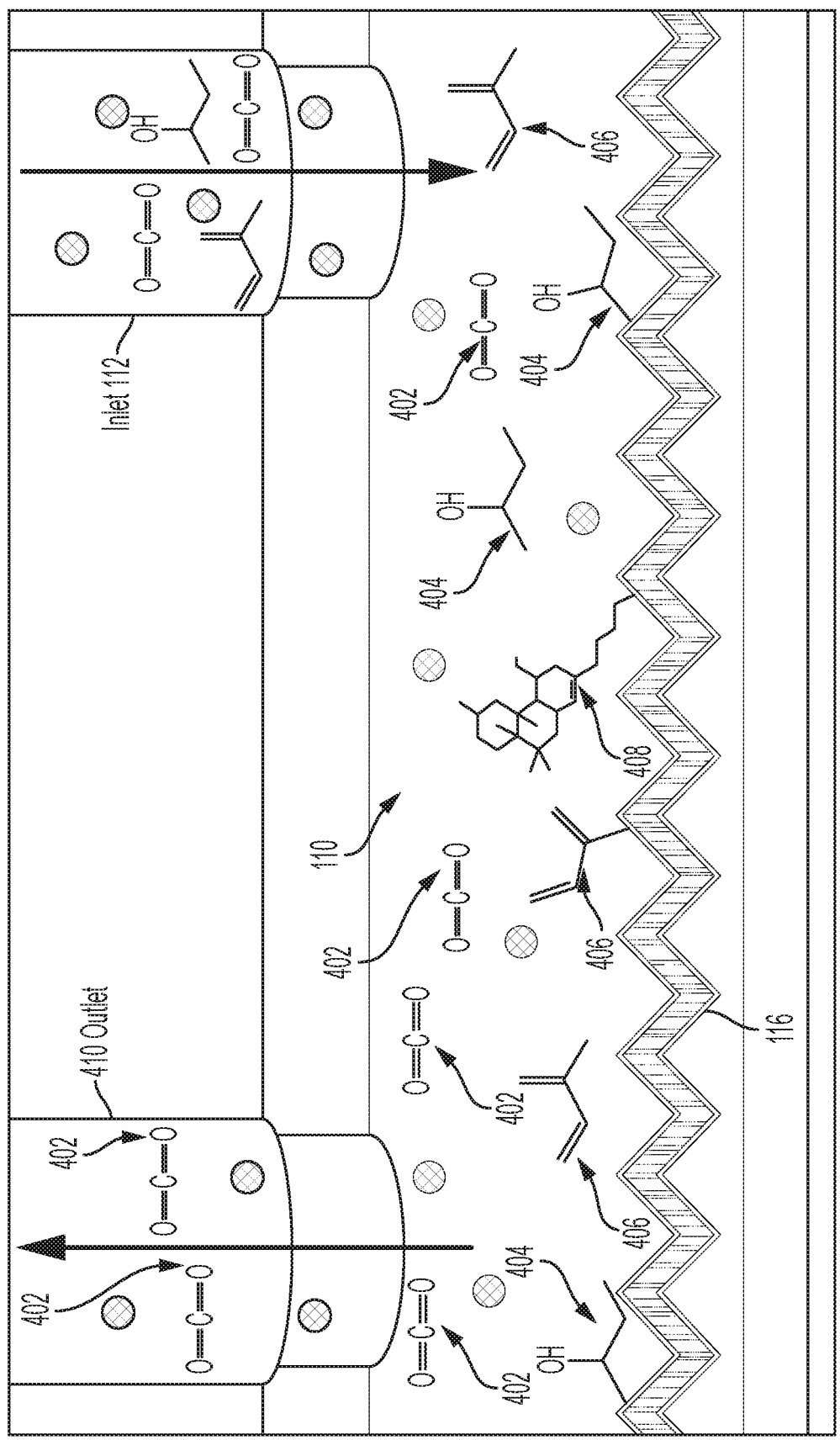
FIG. 4A is a diagram illustrating aspects of receiving a breath sample in a system configured in accordance with aspects of the present disclosure.
Figure 4B:
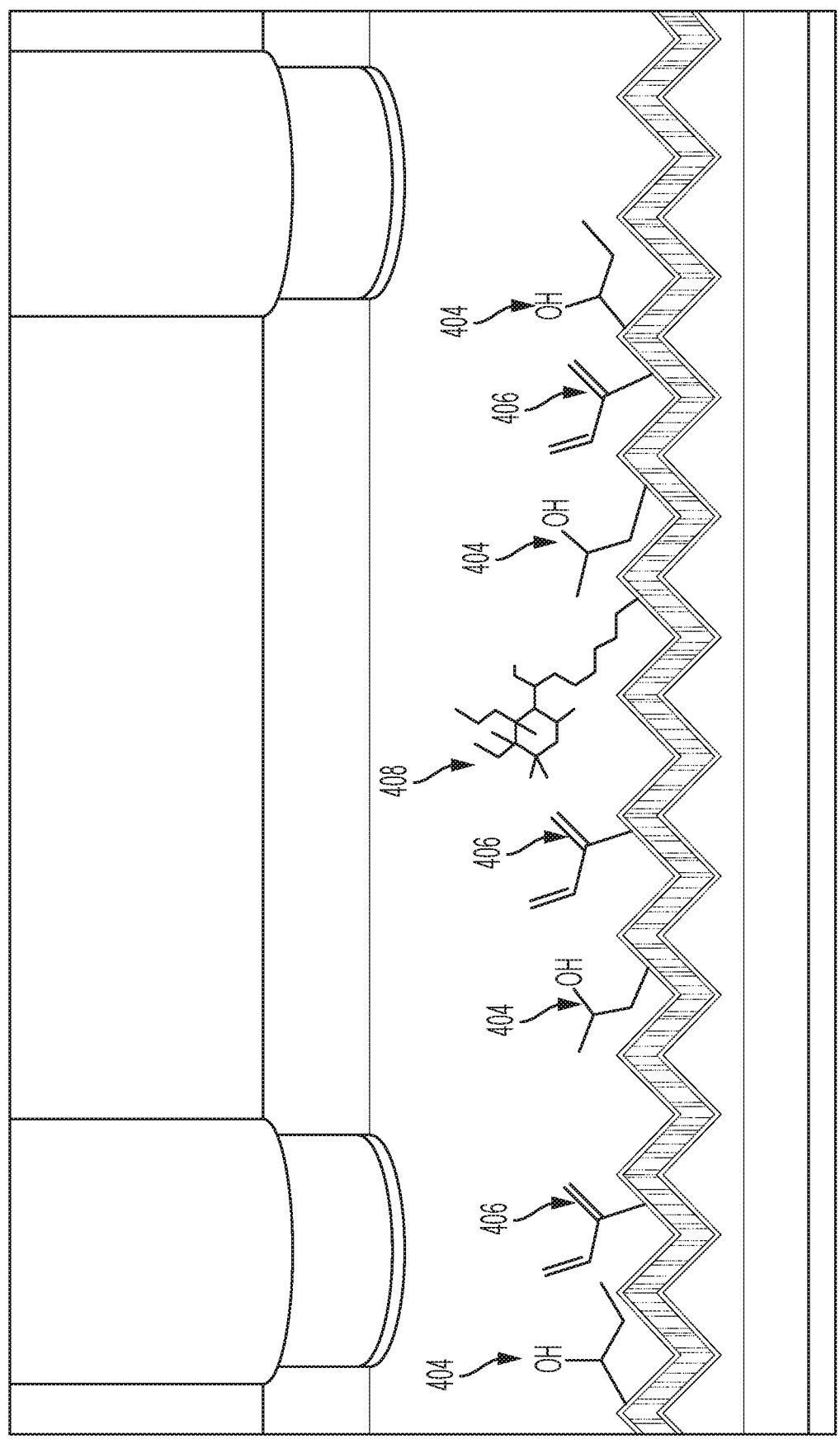
FIG. 4B is a diagram illustrating aspects the behavior of breath sample molecules received in a system configured in accordance with aspects of the present disclosure.
Figure 4C:
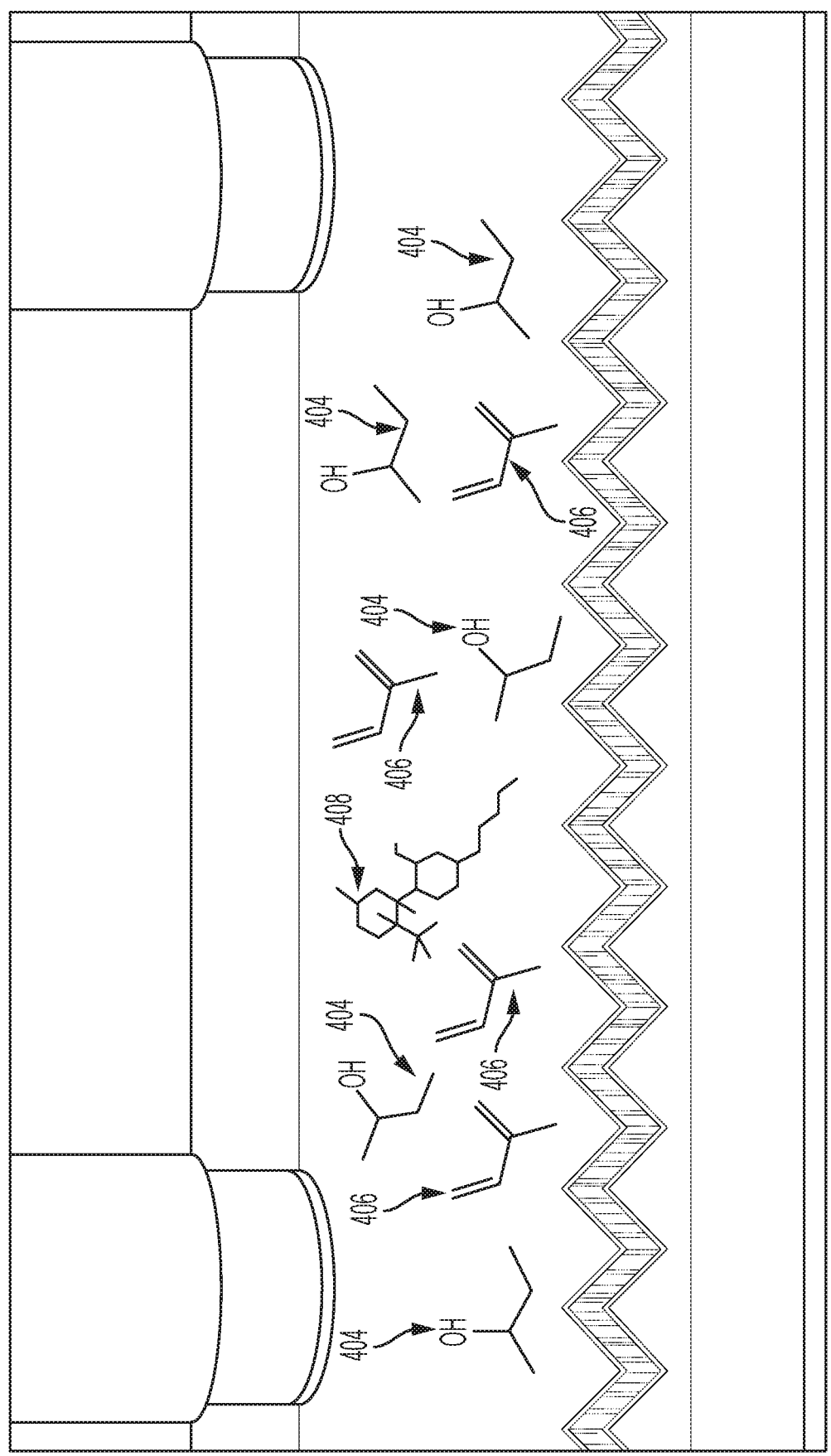
FIG. 4C is a diagram illustrating aspects of analyzing breath sample molecules using a mass spectrometer-based system configured in accordance with aspects of the present disclosure.
Figure 4D:
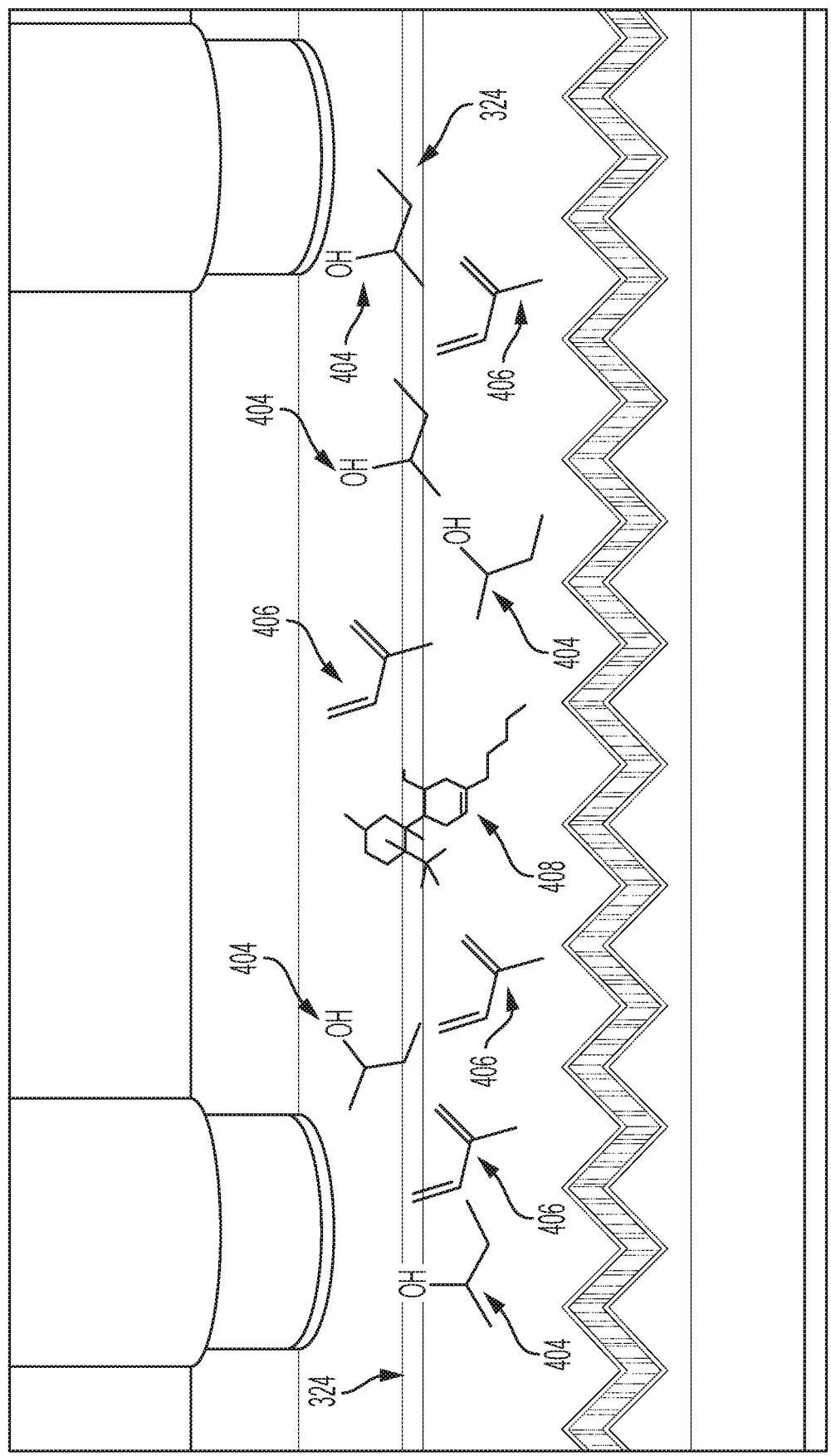
FIG. 4D is a diagram illustrating aspects of analyzing breath sample molecules using a Terahertz (THz) spectrometer-based system configured in accordance with aspects of the present disclosure.

Referring to FIGS. 4A-4D, various aspects of systems for analyzing VOCs present in breath samples in accordance with aspects of the present disclosure are shown. As shown in FIG. 4A, a breath sample may be provided to the sampling chamber 110 via the inlet 112. The breath sample may include one or more VOCs, such as the exemplary VOCs 404, 406, 408 shown in FIG. 4A. Additionally, the breath sample may include non-VOCs, which may include other gases, such as $CO_2$ 402. In an aspect, the sampling chamber 110 may include an outlet 410 configured to release non-VOCs from the sampling chamber 110. It is noted that the outlet 410 is not the same as the outlet 204 of FIG. 2. As shown in FIG. 4B, the VOCs 404, 406, 408 present in the breath sample may adhere to the molecule collector 116. In FIG. 4C, the heating element 118 (not shown in FIGS. 4A-4D) has been activated, introducing heat within the sampling chamber 110, which causes the VOCs to release from the molecule collector 116. After the VOCs are released from the molecule collector 116, the VOCs (or at least a portion of the VOCs) may be provided to a mass spectrometer-based analysis device, such as the analysis device illustrated in FIG. 2, via outlet 204 (not shown in FIG. 4C), for analysis, as described above with reference to FIG. 2. In FIG. 4D, the heating element 118 (not shown in FIGS. 4A-4D) has been activated, introducing heat within the sampling chamber 110, which causes the VOCs to release from the molecule collector 116. After the VOCs are released from the molecule collector 116, the VOCs (or at least a portion of the VOCs) may be provided to a THz spectrometer-based analysis device, such as the analysis device illustrated in FIG. 3, for analysis, as described above with reference to FIG. 2. For example, as illustrated in FIG. 4D, the excitation signal 324 may be provided or projected within the sampling chamber. As described below, excitation of the VOCs by the excitation signal 324 may be utilized by the detector 322 to identify one or more target VOCs present in the breath sample provided to sampling chamber 110.

It is noted that THz spectrometer based systems may provide several advantages over existing systems. For example, using a THz spectrometer may facilitate rapid analysis of breath samples, which may be completed in a matter of seconds, and may facilitate a portable system that can be transported in a local law enforcement vehicle. Additionally, THz spectroscopy-based systems are able to differentiate between Δ-9-THC and CBD because the bonds in the molecules are different. THz spectroscopy or far-infrared spectroscopy may be used to identify compounds that have dipoles that contain a rotational motion. The spectroscopic range is in-between the microwave and infra-red region operating at is between 3 mm-30 μm or 0.1-10 THz. Another advantageous aspect of THz spectrometer-based systems is the granularity at which compounds, such as VOCs, may be identified. For example, THz time domain spectroscopy (THz-TDS) is capable of detecting compounds with concentrations as low as parts-per-trillion. THz-TDS works by emitting a pulsed femtosecond laser, which may be a Ti:Sapphire laser. The laser is sent to two photoconductive antennas after being split in a delay line, resulting a probe beam and a pump beam. The pump beams excites a non-linear crystal, which may formed from gallium arsenide (GaAs), and focuses the signal to the sampling space, such as the volume within the sampling chamber 110. The probe beam sends a signal to the second photoconductive antenna, which detects the THz radiation. To obtain a spectrum of a sample a blank must be taken before the sample, which acts as a reference to subtract from the THz spectra of the sample. THz-TDS is useful in determining the torsional deformations of molecules and the intermolecular bonding of molecules. The benefit of analyzing a gas phase compound, such as breath, is that intermolecular bonding interactions are weaker in the gas phase, leaving only the torsional and rotational spectroscopy signal. One challenge faced by THz-TDS for gas analysis is the large presence of water in the atmosphere, which may alter the device's accuracy depending on the altitude of the device. This issue may be overcome by the collection of background before analysis and with the use of a vacuum or a dry inert gas, such as helium, which removes the water in the signal.

The signal of cannabinoids in the breath may be too low for detection via THZ-TDS, however a pre-concentrator may be used to achieve a suitable signal. Previously, pre-concentration devices have been utilized in the analysis of Δ-9-THC using LC/MS. However, those pre-concentration devices utilized sorbent trapping materials which retain water and impair identification of volatile organic compounds (VOCs). To overcome this challenge, the molecule collector 116 described above may utilize carbon molecular sieves, which reduce the amount of water uptake when looking for VOCs. Carbon molecular sieves work by trapping the compound between graphitic planes, allowing molecules to diffuse fast or slow based on the size of the molecule. The molecules can be rapidly emitted when a heating element is applied to the sorbent material as the graphitic planes enlarge. As described above, in the systems of the present disclosure, a conductive material formed from or coated with a carbon molecular sieve sorbent material may be used as the molecule collector. Based on the type of sorbent material, however, the material may release the VOCs at a different rate, allowing a separation to still be achieved. This process of desorption distinguishes certain carbon molecular sieves materials from others in rapid gas analysis techniques. In aspects, the molecule collector 116 may be formed form a VOC desorptive material, such as Carboxen® (e.g., Carboxen® 1000). Carboxen® may be used in rapid VOC gas analysis to identify specific molecules based on emission time. Larger molecules may not be emitted from the graphitic plane faster than the smaller molecules, allowing the smaller compounds to desorb and be analyzed faster than the larger molecules.

In the description that follows, a THz spectroscopy-based system for cannabinoid detection similar to the system described above with reference to FIG. 3, was cross-referenced with a Thermo Fischer PolarisQ mass spectrometer-based system similar to the system described above with reference to FIG. 2. In the experimental setup, a sampling chamber containing a molecule collector formed from a Carboxen® 1000 coated mesh was coupled to a heating element (e.g., a 24-volt power supply). With a valve connecting an inlet and replaceable mouthpiece to the sampling chamber open, a person would exhale a breath into the sampling chamber, trapping the VOCs on the Carboxen® molecule collector. Other VOCs also adhered to the molecule collector, while non-VOC gases flowed over and out of the sampling tube (FIG. 4A). After completion of the exhale, the valve was closed to prevent any extraneous compounds from depositing onto the molecule collector (FIG. 4B). The molecule collector was then supplied with 24 volts to evenly heat the molecule collector and promote rapid desorption of the compounds adhered thereto. For mass spectrometry reference characterization, the released compounds were provided to the mass spectrometer for a signal to be detected (FIG. 4C). Being formed from Carboxen®, the molecule collector also facilitated a separation technique, where smaller VOCs were emitted faster than larger compounds. This enabled a determination of the proper time at which the cannabinoids were emitted from the molecule collector. Once the proper time was determined, the THz spectrometer was used to determine the presence of cannabinoids without the presence of other background signals, aiding in an accurate and precise measurement. Once this time reference of cannabinoids was collected, the sampling chamber was placed in the THz spectrometer-based analysis device, allowing the excitation signal (e.g., a THz laser signal) to be used to detect the samples emitted by the molecule collector (FIG. 4D). The THz spectrometer-based system may act in two manners. The first being that the compounds (e.g., the VOCs) may be emitted from the molecule collector and then be excited via the excitation signal. The excited molecule(s) may then be detected as an absorbance by the detector as it returns to ground state. The other mechanism would be that excitation of the molecule(s) due to the rapid heating of the molecule collector may result in a fluorescent signal being emitted. The system may be configured to determine the presence of cannabinoids and/or other VOCs in the breath sample based on the fluorescent signal emitted in response to the excitation of the VOCs by the excitation signal.

Figure 5:
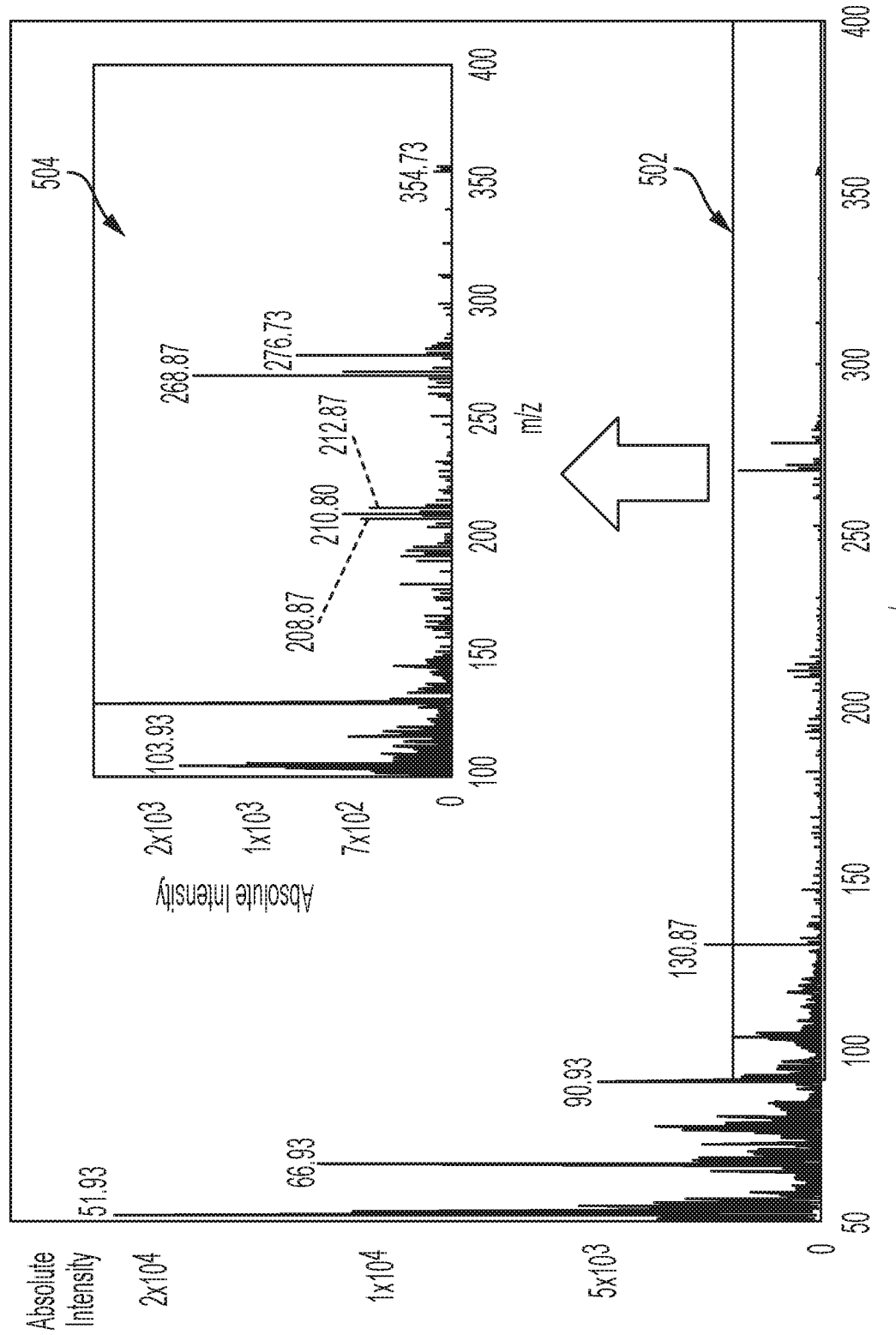
FIG. 5 is a graph illustrating observed VOCs for a healthy breath sample.
Figure 6:
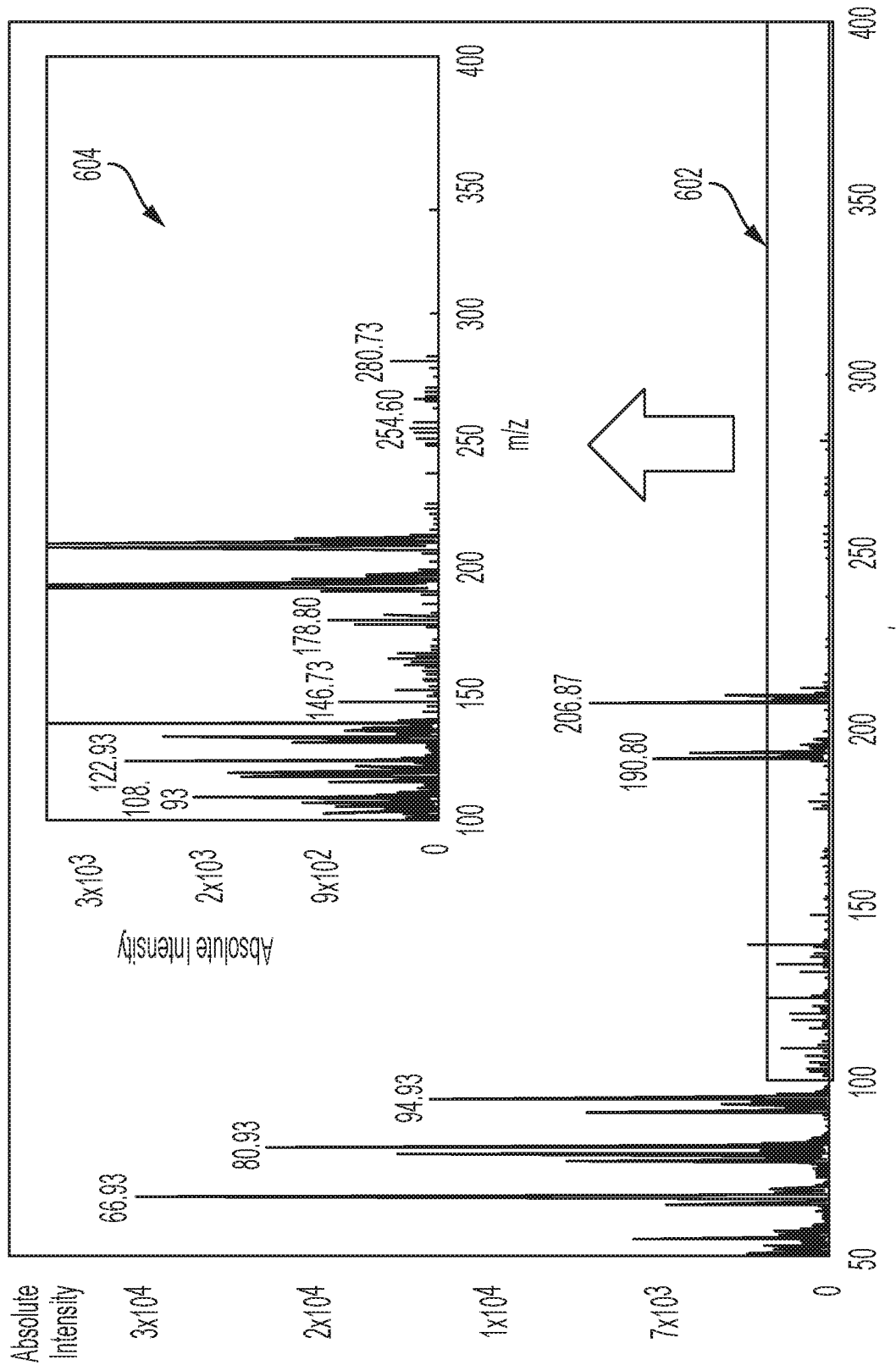
FIG. 6 is a graph illustrating observed VOCs for a breath sample of a person suffering from seasonal allergies.
Figure 7:
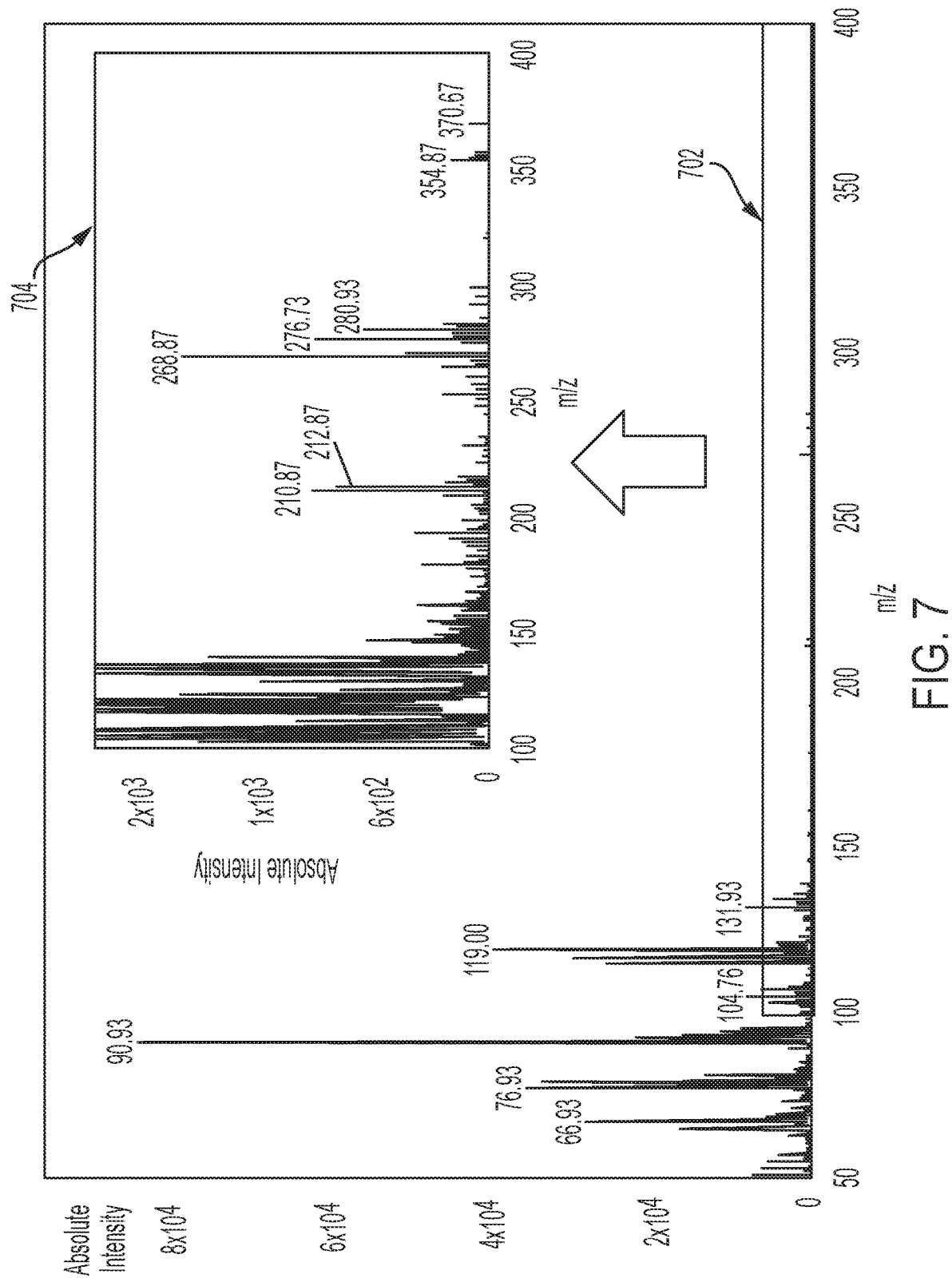
FIG. 7 is a graph illustrating observed VOCs for a breath sample of a person after using mouthwash.

A mass spectrometer-based system was developed and utilized to analyze breath samples. Using this system, differences in the physical state of a person exhaling have already been demonstrated. Healthy breath samples, breath samples from a person suffering from seasonal allergies (allergy breath), and breath samples obtained from a person directly after washing their mouth out with Listerine were collected in sampling chambers having a molecule collector formed from a Carboxen® coated mesh attached to a PolarisQ ion trap mass spectrometer. The results of the analysis performed on each of the breath samples are illustrated in FIG. 5 (healthy breath sample), FIG. 6 (breath sample of a person suffering from seasonal allergies), and FIG. 7 (breath sample from a person directly after washing with Listerine). In FIG. 5, cutout 504 illustrates an enlarged view of the peaks illustrated in box 502. In FIG. 6, cutout 604 illustrates an enlarged view of the peaks illustrated in box 602. In FIG. 7, cutout 704 illustrates an enlarged view of the peaks illustrated in box 702. As shown in FIG. 5, a large 51.93 m/z value was observed, which corresponds to 1-buten-3-yne. This 1-buten-3-yne was not found in the allergy breath sample. In the allergy breath sample, the largest peak was observed at 66.93 m/z, which corresponds to isoprene, followed by peaks at 80.93 m/s (1-methyl-pyrrole) and 94.93 m/z (2-ethylpyrrole), as shown in FIG. 6. In the mouthwash sample, illustrated in FIG. 7, the peak associated with isoprene was lowered, as expected, and other peaks were established, such as the ethylmethylsulfide peak at 76.93 m/z and 1,2,3-propanetriol at 90.93 m/z. Furthermore, larger molecular weight compounds became present, such as the octadecane peak at 254.60 m/z, illustrated in cutout 604. The samples all show a prominent 66.93 m/z peak, which denotes isoprene. Isoprene should be found in all breath samples and may be used as a reference to ensure that the instrument is sampling the breath VOCs. As shown in FIGS. 5-7, prominent changes in the observed compounds were be found in the three different scenarios presented. Utilizing this instrument as a reference, determination of cannabinoids in breath samples was achieved using the terahertz spectrometer, as described below.

Figure 8:
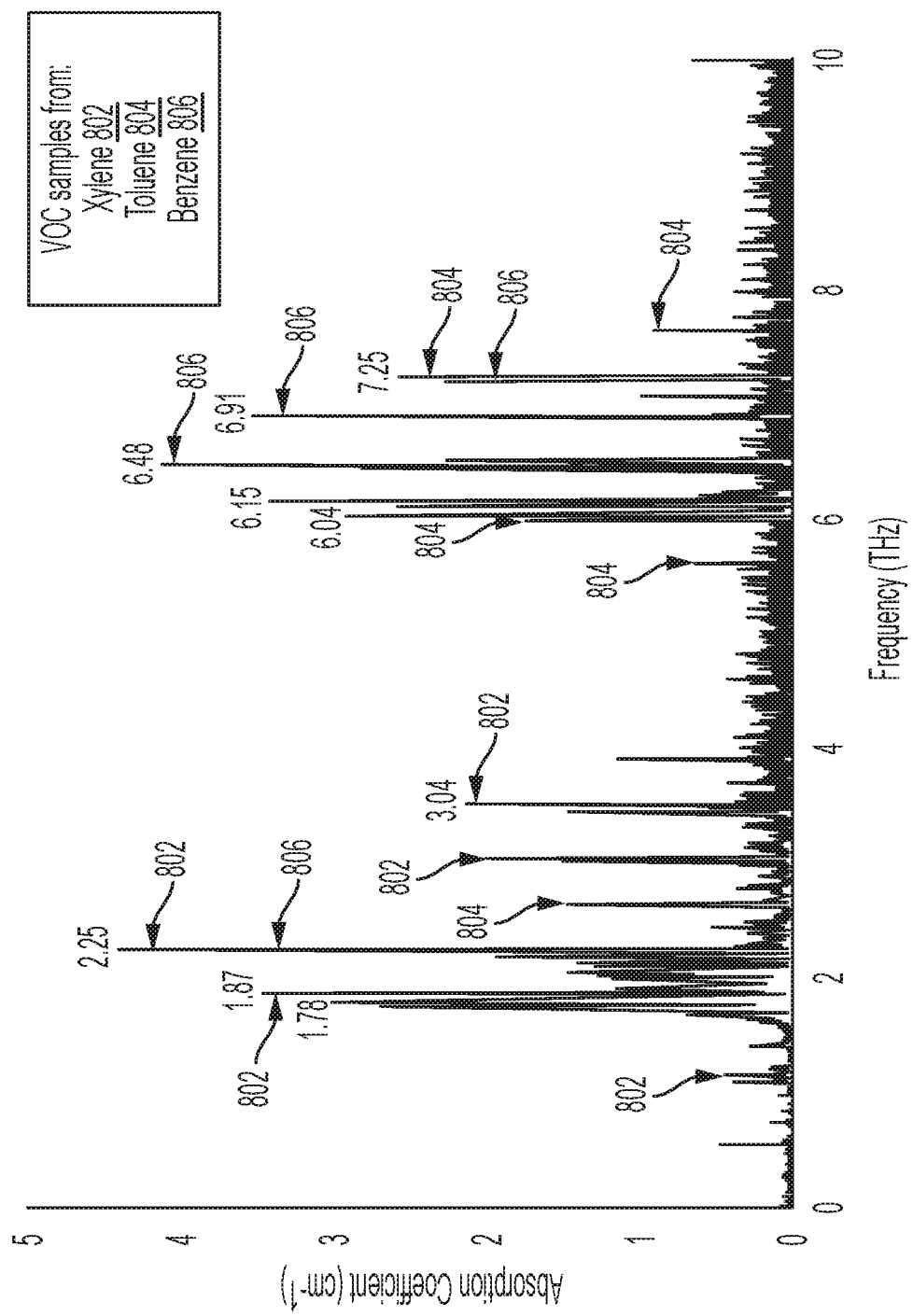
FIG. 8 is a graph illustrating observed VOCs for toluene, benzene, and xylene.
Figure 9:
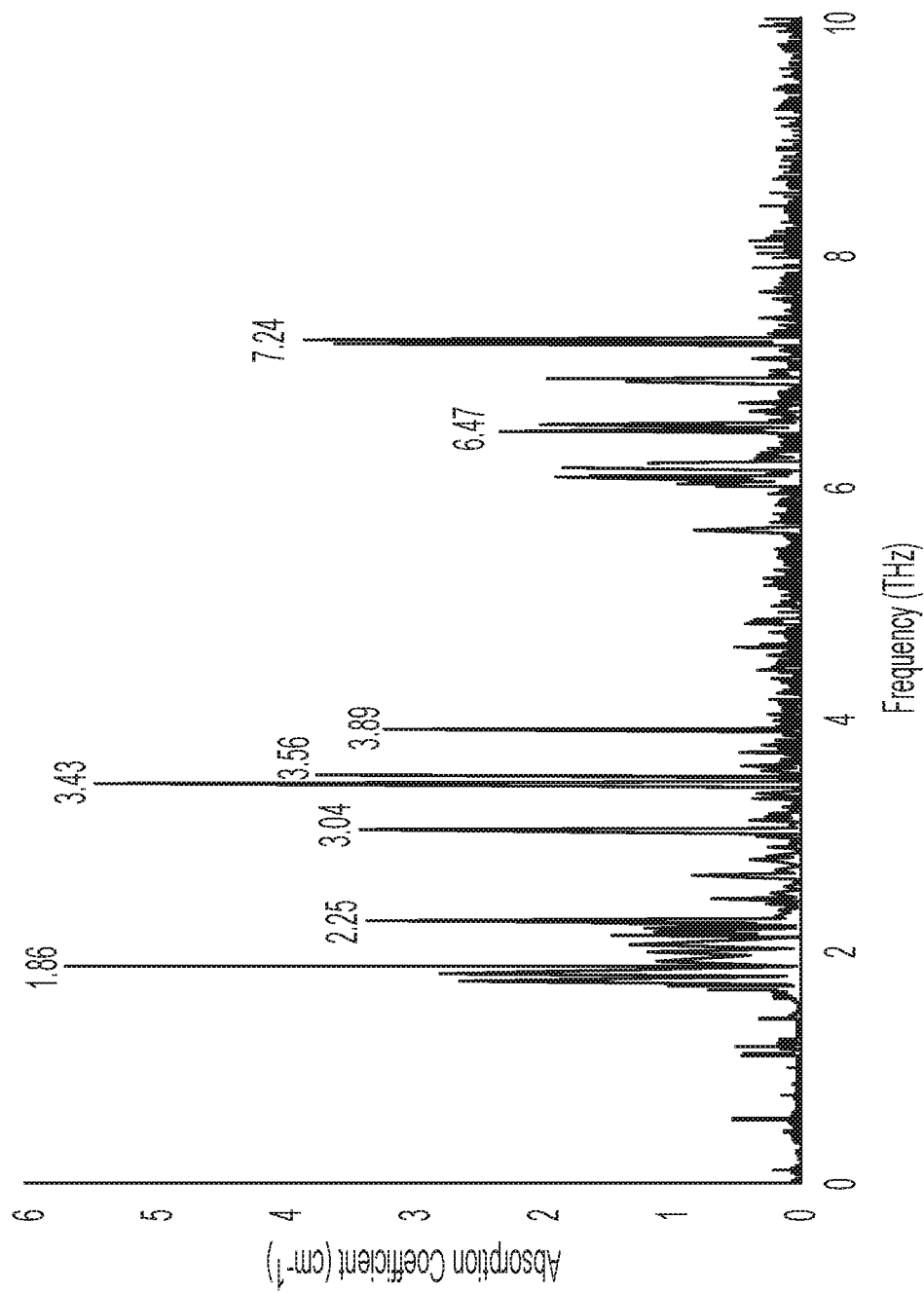
FIG. 9 is a graph illustrating observed VOCs for a marijuana sample.

The terahertz spectra of benzene, toluene, and xylene were acquired and compared to the terahertz spectra of a gas sample of heated marijuana leaves using a MenloSystems (Martinsried, Germany) K15 Time Domain Terahertz Spectrometer. This instrument was used to pump a dry gas, Helium, into a flask, forcing the volatile vapors out and into the sampling chamber where the VOCs adhered to a Carboxen®-based molecule collector. A voltage was then applied to the molecule collector, releasing the VOCs. The results observed for benzene, toluene, and xylene are illustrated in FIG. 8, where lines 802 represent VOCs resulting from xylene, lines 804 represent VOCs resulting from toluene, and lines 806 represent VOCs from benzene. FIG. 9 illustrates VOCs observed from the marijuana sample. The analysis of the gaseous samples allowed the rotational spectroscopy to be obtained, explaining the low signal obtained for benzene at any of the frequencies scanned. The marijuana sample resulted in the most number of rotational bonds, which is to be expected as it was not a pure sample. The xylene and toluene appeared to be the same peak, however the xylene consistently resulted in a lower frequency peak, while the toluene appeared at a higher frequency. This is because xylene has two methyl groups attached to the aromatic ring, while the toluene only has one methyl group attached to the aromatic ring.

Methods to quantitate gas based on terahertz spectra have been done using cigarette smoke using continuous wave terahertz spectroscopy. However, to do so a database to input variables for the Lorentzian fit equation is required. Cannabinoids have not yet been databased, preventing the Lorentzian fit equation from being useful in cannabinoid quantitation. However, quantitation can still be achieved using the absorbance coefficient of the terahertz spectra. Based on the transmission of the sample THz field compared to the transmission field the measured transmission t(f), the absorbance coefficient can be calculated as:

$$n_s(f) = 1 - \frac{c\phi(f)}{2\pi f d}, \tag{1}$$

were ns(f) is the sample refractive index, c us the speed of light in a vacuum, ϕ(f) is the phase difference between the transmission of the sample terahertz field and the transmission of the reference terahertz field, f is the frequency, and d is the sample thickness. The sample thickness may be the length of the sampling chamber, which was 9 cm in the above-described examples. The sample refractive index, expressed as:

$$\alpha(f) = -\frac{2}{d}\ln\frac{|t(f)|}{RL}, \tag{2}$$

$$RL = \frac{4n_s}{(1+n_s)^2}, \quad (3)$$

may be calculated the absorption coefficient α(f) can be calculated, where the loss of signal at the interface is equal to RL. Subtracting the sample spectra from the reference spectra allows the Beer-Lambert law to be used as follows:

$$\alpha(f) = -\frac{\ln T(f)}{d}, \quad (4)$$

where T(f) is equal to the ratio between the intensity of the sample transmitted THz field and the reference transmitted THz field. This may allow for a rapid quantitation of Δ-9-THC. A breath sample analyzer system in accordance with the present disclosure may be configured (e.g., via software stored as instructions) to utilize these equations to calculate the concentration of cannabinoids from the breath of the person. The sample volume may change from person to person. Accordingly, the system may be configured to take the overall volume of the breath sample that the person has exhaled into consideration so as to avoid or mitigate inaccuracies in the determined concentration.

Figure 10:
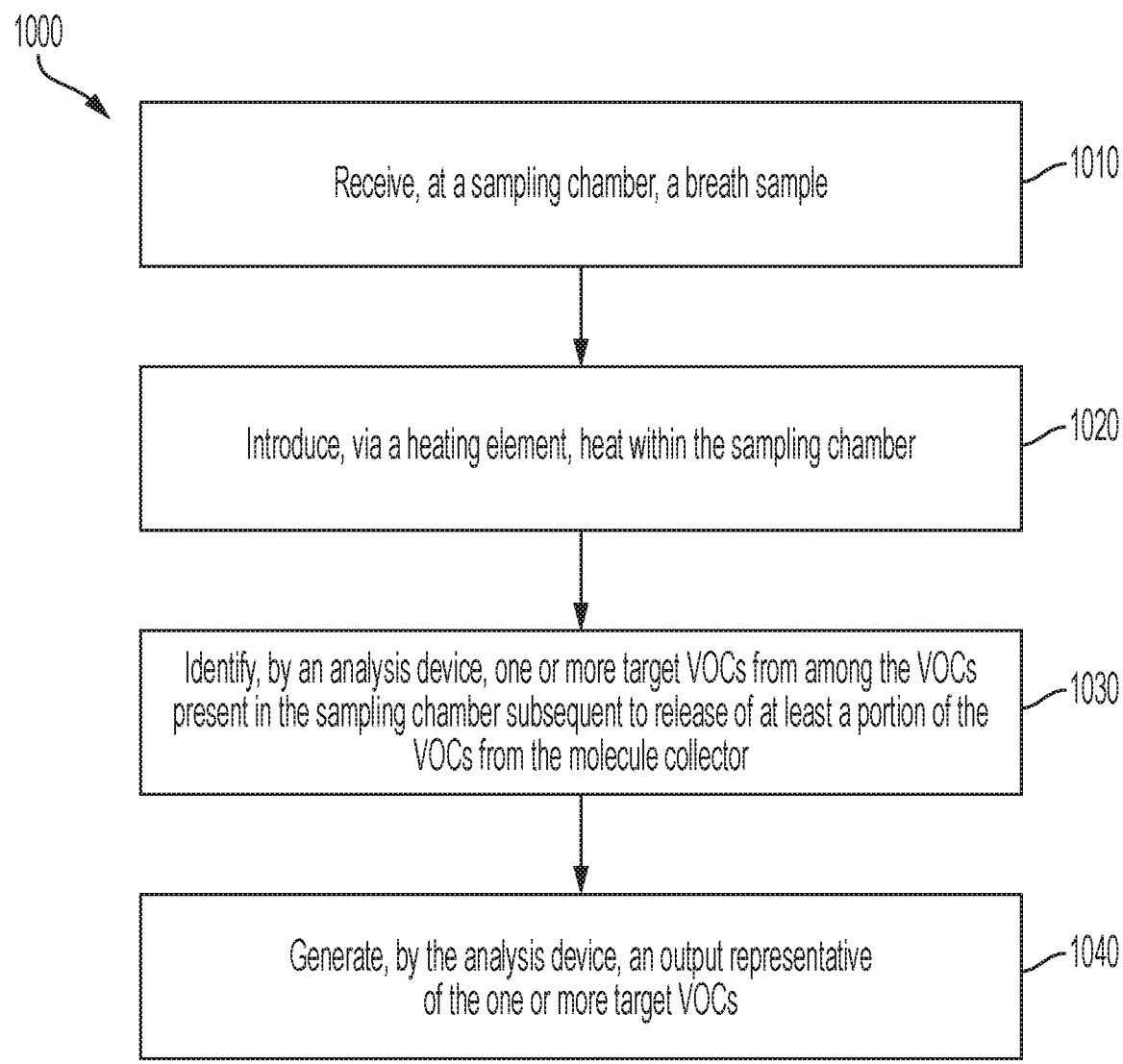
FIG. 10 is a flow diagram of a method for analyzing a breath sample in accordance with aspects of the present disclosure.

Referring to FIG. 10, a flow diagram of a method for analyzing a breath sample in accordance with aspects of the present disclosure is shown as a method 1000. In an aspect, the method 1000 may be performed by the system 100 of FIG. 1, which may utilize a mass spectrometer-based approach, as described above with reference to FIG. 2 or a THz spectrometer-based approach, as described above with reference to FIG. 3. In an aspect, operations or steps of the method 100 may be realized as a program or instructions (e.g., the instructions 132 of FIGS. 1-3) stored at a memory (e.g., the memory 130 of FIGS. 1-3) that, when executed by one or more processors (e.g., the one or more processors 122 of FIG. 1-3), cause the one or more processors to perform operations for analyzing a breath sample in accordance with aspects of the present disclosure.

As shown in FIG. 10, the method 1000 includes, at step 1010, receiving, at a sampling chamber, a breath sample. As described above, the breath sample may be received at the sampling chamber via an inlet (e.g., the inlet 112 of FIG. 1) coupled to the sampling chamber (e.g., the sampling chamber 110 of FIG. 1) and the sampling chamber may include a molecule collector (e.g., the molecule collector 116 of FIG. 1) disposed within the sampling chamber. At step 1020, the method 1000 includes introducing, via a heating element, heat within the sampling chamber. In an aspect, the heat may be introduced by the heating element 118 of FIG. 1. At step 1030, the method 1000 includes identifying, by an analysis device, one or more target VOCs from among the VOCs present in the sampling chamber subsequent to release of at least a portion of the VOCs from the molecule collector. As described above, at least the portion of the VOCs may be released from the molecule collector by the heat introduced within the sampling chamber by the heating element (e.g., at step 1020). The analysis device may be a mass spectrometer-based device, as described above with reference to FIG. 2, or may be a THz spectrometer-based device, as described above with reference to FIG. 3. At step 1040, the method 1000 includes generating, by the analysis device, an output representative of the one or more target VOCs. In an aspect, the one or more target VOCs may be associated with one or more of Δ-9-THC, 11-hydroxy-tetrahydrocannabinol (11-OH-THC), carboxy-tetrahydrocannabinol (THC-COOH), THC metabolites, opioids (e.g., methadone and fentanyl, opioid metabolites). As described above, the output representative of the one or more target VOCs may include information that quantitates a concentration of the one or more target VOCs with respect to a source of the breath sample, such as a person providing the breath sample.

As shown above, breath analysis systems and methods in accordance with the present disclosure may provide devices that facilitate detection of cannabinoids and other substances from breath samples in the field. Such systems may be utilized by law enforcement personnel to rapidly and accurately identify/determine whether drivers are DUIM. The ability to make such determinations in the field greatly enhances the capabilities of the criminal justice field with respect to detecting and addressing this issue. For example, previous techniques required a sample to be obtained and then sent to a lab, taking minutes or hours. This long analysis time prevents any action from being properly taken at the scene of the event. In contrast, utilizing breath analysis systems in accordance with the present disclosure, local law enforcement agents can obtain conclusive evidence on scene. This application of the instrument challenges other fields to shift towards furthering the detection of DUIM drivers, removing them from the roads, and enhancing the safety of other drivers. Additionally, the breath analysis systems of the present disclosure may facilitate detection of other illicit drugs with rapid and portable techniques. In addition to detection in the field, the ability to accurately quantitate the concentration of cannabinoids provided by the disclosed systems may provide the ability to develop a standard concentration used to define whether a person is DUIM.

Although embodiments of the present application and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Moreover, the scope of the present application is not intended to be limited to the particular embodiments of the process, machine, manufacture, composition of matter, means, methods and steps described in the specification.

The invention claimed is:
1. A system for analyzing a breath sample, the system comprising:
a sampling chamber;
an inlet coupled to the sampling chamber and configured to receive a breath sample and to provide the breath sample to the sampling chamber;

a molecule collector disposed within the sampling chamber, wherein the molecule collector is configured to adhere to volatile organic compounds (VOCs) present in the breath sample;

a heating element configured to introduce heat within the sampling chamber; wherein at least a portion of the VOCs are released from the molecule collector based on the heat introduced within the sampling chamber by the heating element;

an analysis device comprising a Terahertz (THz) spectrometer that includes an excitation source and a detector, wherein the analysis device is configured to:
  introduce, via the excitation source, an excitation signal within the sampling chamber subsequent to the release of at least a portion of the VOCs from the molecule collector;
  identify, via the detector, one or more target VOCs from among the VOCs present in the sampling chamber subsequent to release of at least a portion of the VOCs from the molecule collector, wherein the one or more target VOCs are identified based on one or more characteristics associated with excitation of at least the portion of the VOCs released from the molecule collector in response to the excitation signal; and
  generate an output representative of the one or more target VOCs.

2. The system of claim 1, wherein the molecule collector comprises a Carboxen® coated mesh or other carbon molecular sieve.

3. The system of claim 1, wherein the heating element comprises a power source coupled to the molecule collector and configured to apply a voltage to the molecule collector to introduce the heat within the sampling chamber.

4. The system of claim 1, wherein the excitation source comprises a THz laser, and wherein the one or more target VOCs include Δ-9-THC, 11-hydroxy-tetrahydrocannabinol (c11-OH-THC), carboxy-tetrahydrocannabinol (THC-COOH), THC metabolites, opioids, opioid metabolites, or a combination thereof.

5. The system of claim 1, wherein the one or more characteristics associated with the excitation of at least the portion of the VOCs comprises at least one of: an absorbance characteristic and a fluorescent emission characteristic.

6. The system of claim 1, further comprising a disposable mouthpiece removably coupled to a first end of the inlet, wherein a second end the inlet is coupled to the sampling chamber.

7. The system of claim 1, further comprising a valve disposed within an air flow path between the inlet and the sampling chamber, wherein the valve is configurable to at least a first state and a second state, the first state corresponding to an open state configured to allow the breath sample to flow into the sampling chamber and the second state corresponding to a closed state configured to prevent contamination of the breath sample.

8. The system of claim 1, further comprising an outlet configured to release non-VOCs from the sampling chamber.

9. The system of claim 1, wherein the output representative of the one or more target VOCs comprises information that quantitates a concentration of the one or more target VOCs with respect to a source of the breath sample.

10. The system of claim 1, further comprising a sensor configured to determine whether the breath sample satisfies one or more criterion.

11. A method for analyzing a breath sample, the method comprising:
  receiving, at a sampling chamber, a breath sample via an inlet coupled to the sampling chamber, wherein the sampling chamber comprises a molecule collector disposed within the sampling chamber, and wherein the molecule collector is configured to adhere to volatile organic compounds (VOCs) present in the breath sample;
  introducing, via a heating element, heat within the sampling chamber, wherein at least a portion of the VOCs are released from the molecule collector based on the heat introduced within the sampling chamber;
  detecting, by an analysis device, one or more target VOCs from among the VOCs present in the sampling chamber subsequent to release of at least a portion of the VOCs from the molecule collector, wherein the analysis device comprises a Terahertz (THz) spectrometer and the detecting comprises:
    emitting, by an excitation source, an excitation signal within the sampling chamber subsequent to the release of at least the portion of the VOCs from the molecule collector; and
    identifying, by a detector of the THz spectrometer, the one or more target VOCs based on one or more characteristics associated with excitation of at least the portion of the VOCs released from the molecule collector in response to the excitation signal; and
  generating, by the analysis device, an output representative of the one or more target VOCs, wherein the output representative of the one or more target VOCs comprises information that quantitates a concentration of the one or more target VOCs with respect to a source of the breath sample.

12. The method of claim 11, wherein the molecule collector comprises a Carboxen® coated mesh, wherein the heating element comprises a power source coupled to the molecule collector, and wherein the method comprises applying a voltage to the molecule collector to introduce the heat within the sampling chamber.

13. The method of claim 11, wherein the one or more target VOCs include Δ-9-THC, 11-hydroxy-tetrahydrocannabinol (11-OH-THC), carboxy-tetrahydrocannabinol (THC-COOH), THC metabolites, opioids, opioid metabolites, or a combination thereof.

14. The method of claim 11, wherein the excitation source comprises a THz laser, and wherein the one or more characteristics associated with the excitation of at least the portion of the VOCs comprise at least one of: an absorbance characteristic and a fluorescent emission characteristic.

15. A non-transitory computer-readable storage medium storing instructions that, when executed by one or more processors, cause the one or more processors to perform operations for analyzing a breath sampe, the operations comprising:
  activating a heating element configured to introduce heat within a sampling chamber subsequent to a breath sample being provided to the sampling chamber, wherein the sampling chamber comprises a molecule collector disposed within the sampling chamber, wherein the molecule collector is configured to adhere to volatile organic compounds (VOCs) present in the breath sample, and wherein at least a portion of the VOCs are released from the molecule collector based on the heat introduced within the sampling chamber;
  detecting, by an analysis device, one or more target VOCs from among the VOCs present in the sampling chamber subsequent to release of at least a portion of the VOCs from the molecule collector, wherein the analysis device comprises a Terahertz (THz) spectrometer and the detecting comprises:

controlling an excitation source to emit an excitation signal within the sampling chamber subsequent to the release of at least the portion of the VOCs from the molecule collector; and Identifying, by a detector of the THz spectrometer, the one or more target VOCs based on one or more characteristics associated with excitation of at least the portion of the VOCs released from the molecule collector in response to the excitation signal, wherein the one or more target VOCs include Δ-9-THC, 11-hydroxy-tetrahydrocannabinol (11-OH-THC), carboxy-tetrahydrocannabinol (THC-COOH), THC metabolites, opioids, opioid metabolites, or a combination thereof; and generating an output representative of the one or more target VOCs, wherein the output representative of the one or more target VOCs comprises information that quantitates a concentration of the one or more target VOCs with respect to a source of the breath sample.

\* \* \* \* \*

UNITED STATES PATENT AND TRADEMARK OFFICE
CERTIFICATE OF CORRECTION

PATENT NO. : 10,813,585 B2
APPLICATION NO. : 16/715576
DATED : October 27, 2020
INVENTOR(S) : Guido Fridolin Verbeck, IV et al.

It is certified that error appears in the above-identified patent and that said Letters Patent is hereby corrected as shown below:

In the Claims

At Column 15, Claim number 1, Line number 6, delete "chamber;" and replace with --chamber,--.
At Column 15, Claim number 4, Line number 38, delete "(c11-OH-THC)" and replace with --(11-OH-THC)--.
At Column 16, Claim number 15, Line number 54, delete "breath sampe" and replace with --breath sample--.
At Column 17, Claim number 15, Line number 9, delete "Identifying" and replace with --identifying--.

Signed and Sealed this
Twelfth Day of January, 2021

Andrei Iancu
*Director of the United States Patent and Trademark Office*